(12) United States Patent
Hengerer et al.

(10) Patent No.: US 8,386,017 B2
(45) Date of Patent: Feb. 26, 2013

(54) METHOD FOR IMPLEMENTING AN IMAGING EXAMINATION METHOD

(75) Inventors: Arne Hengerer, Erlangen (DE); Sebastian Schmidt, Weisendorf (DE); Carsten Warmuth, Berlin (DE)

(73) Assignee: Siemens Aktiengesellschaft, Munich (DE)

( * ) Notice: Subject to any disclaimer, the term of this patent is extended or adjusted under 35 U.S.C. 154(b) by 572 days.

(21) Appl. No.: 12/458,761

(22) Filed: Jul. 22, 2009

(65) Prior Publication Data

US 2010/0022870 A1    Jan. 28, 2010

(30) Foreign Application Priority Data

Jul. 23, 2008  (DE) .................. 10 2008 034 313

(51) Int. Cl.
*A61B 5/055*    (2006.01)
*A61B 5/02*    (2006.01)
(52) U.S. Cl. .................. 600/420; 600/419; 600/504
(58) Field of Classification Search ............ 600/410, 600/419, 420, 504; 378/4
See application file for complete search history.

(56) References Cited

U.S. PATENT DOCUMENTS 6,654,628 B1 *   11/2003   Silber et al. ............. 600/410
2010/0249620 A1 *   9/2010   Cho ........................ 600/504

FOREIGN PATENT DOCUMENTS

DE    102004059133 A1    7/2006

OTHER PUBLICATIONS

Frauenfelder et al. in Flow and wall shear stress in end-to-side and side-to-side anastomosis of venous coronary artery bypass grafts, BioMedical Engineering OnLine 2007, 6:35; Others.
Taupitz, Matthias et al., "New Generation of Monomer-Stabilized Very Small Superparamagnetic Iron Oxide Particles (VSOP) as Contrast Medium for MR Angiography: Preclinical Results in Rats and Rabbits", Journal of Magnetic Resonance Imaging 12:905-911 (2000); Others.
Taupitz, Matthias et al., "Phase I Clinical Evaluation of Citrate-coated Monocrystalline Very Small Superparamagnetic Iron Oxide Particles as a New Contrast Medium for Magnetic Resonance Imaging", Investigative Radiology, vol. 39, No. 7, Jul. 2004, pp. 394-405; Others.
Zhi-Yong Li et al.: "Simulation of the Interaction between Blood Flow and Atherosclerotic Plaque"; Proceedings of the 29th Annual International Conference of the IEEE EMBS, Cite Internationale, Lyon, France, Aug. 23-26, 2007, p. 1699-1702; Others; 2007; FR.
Claire Corot et al.: "Recent advances in iron oxide nanocrystal technology for medical imaging"; Advanced Drug Delivery Reviews 58 (2006), p. 1471-1504, Science Direct; Others; 2006.

* cited by examiner

*Primary Examiner* — Michael Rozanski
(74) *Attorney, Agent, or Firm* — Harness, Dickey & Pierce, P.L.C.

(57) ABSTRACT

A method is disclosed for implementing an imaging examination method. In at least one embodiment, the method includes creating an overview data record containing angiography data relating to a patient; simulating flow conditions in vessels of the patient; determining a strain on the vascular walls with the aid of the simulation; identifying vascular regions, in which the strain on the vascular wall exceeds a threshold value and implementing an imaging examination in at least one of the identified vascular regions.

10 Claims, 3 Drawing Sheets

METHOD FOR IMPLEMENTING AN IMAGING EXAMINATION METHOD

PRIORITY STATEMENT

The present application hereby claims priority under 35 U.S.C. §119 on German patent application number DE 10 2008 034 313.7 filed Jul. 23, 2008, the entire contents of which are hereby incorporated herein by reference.

FIELD

At least one embodiment of the present invention generally relates to a method for implementing an imaging examination method.

BACKGROUND

Imaging examination methods allow a doctor or radiologist to be able to diagnose a plurality of patient diseases. Many diseases require special examination methods in order to ensure a reliable diagnosis. Imaging diagnosis is gaining increasing importance particularly with the treatment of vascular diseases but also with tumor treatment. With the diagnosis and therapy of arteriosclerosis, it is desirable for instance to be able to quantitatively determine the plaques developing in a vascular system of a patient and which result in arteriosclerosis. It was previously only possible to control individual plaques during the temporal course.

While simple narrowing of the vessel (stenosis) can be identified comparatively easily in angiography, diseases, in which only one pathological change in the vascular wall is present, but still no stenosis, can only be diagnosed when a damaging event has taken place. This is the case for instance if the innermost layer of the vascular wall (intima) has peeled away and has blocked the vessel.

A visualization using the known magnetic resonance tomography (MR) methods is possible with the so-called vulnerable plaques. It is known to use specially prepared iron oxide particles (Very Small Iron Oxide Particles, VSOP; Ultra Small Iron Oxide Particle, USPIO) or Gd- or F-marked liposomes as the contrast agent. The contrast agent can be coupled here to plaque-specific ligands (e.g. uPA, RGD), so that they accumulate in the plaques. A high measurement resolution is needed in order to identify the VSOP accumulation due to the signal deletion and the generally minimal accumulation of the iron oxide content, thereby resulting in long measurement times. A complete examination of a patient is thus generally not possible due to time constraints. The same applies to the use of marked liposomes, which likewise only accumulate to a minimum degree.

On the other hand, it is known to detect the blood flow within a vascular tree by means of numerical simulations. To this end, the shape of the vascular tree has to be known, which may therefore result for instance from a segmented angiography (based on an MR or CT measurement). One example of a method of this type has been described by Frauenfelder et al. in "Flow and wall shear stress in end-to-side and side-to-side anastomosis of venous coronary artery bypass grafts", BioMedical Engineering OnLine 2007, 6:35. Methods, in which the interior of a vessel is examined using a catheter, are likewise known. Further methods for determining the blood flow dynamics are the optical coherence tomography, intravascular ultrasound and near-infrared fluorescence diagnostics.

SUMMARY

At least one embodiment of the present invention specifies a method for implementing an imaging examination method, by which vulnerable plaques in particular can be made visible efficiently.

According to an example embodiment of the invention, a method for implementing an imaging examination method comprises:
  creating an overview data record with angiography data from a patient,
  simulating flow ratios in the vessels of the patient,
  determining a strain on vascular walls on the basis of the simulation
  identifying vascular regions, in which the strain on vascular walls exceeds a threshold value, and
  implementing an imaging examination in at least one of the identified vascular regions.

One basic idea behind an embodiment of the invention resides here in combining already known methods for the more efficient examination of vascular diseases. The automated selection of vascular regions for a more detailed examination enables a more comprehensive examination of the patient in the case of a significantly reduced measurement time. Vascular regions with probably existing vulnerable plaques can thus be determined for instance by way of simulation and selected for a more detailed examination.

In an advantageous embodiment of the invention, several of the identified vascular regions are examined, with the vascular regions being examined in sequence of their overshooting of the threshold value. This is particularly advantageous in the case of patients with a plurality of identified vascular regions. The regions which are potentially most dangerous are preferably examined.

In an advantageous configuration of at least one embodiment of the invention, the measurement time for the examinations of the identified vascular regions is prespecified and a number of examinations of vascular regions which can be implemented during the measurement time is selected. This automatically restricts the number of implemented examinations to the measurement time available, with the regions which are potentially most dangerous firstly being examined by sorting according to the sequence of overshootings of the threshold value. The vascular region with the largest overshootings of the threshold value is examined first, after which follows the vascular region with the second largest overshootings of the threshold etc.

In an advantageous configuration of at least one embodiment of the invention, the overview data record is generated by means of a first MR examination method using a contrast agent containing iron oxide or marked liposomes. Comparatively little resolution can be used here which thereby significantly reduces the measurement time compared with detailed examinations. A region of the patient which is of huge interest can be examined at the same time as a similarly comparatively minimal measurement period.

In an advantageous configuration of at least one embodiment of the invention, the identified vascular regions are examined by way of a second MR examination method, with an additional contrast agent containing iron oxide or a marked liposome being shown. This is preferably the same contrast agent which was also used for creating the overview data record. This also shortens the measurement period and the strain on the patient. To avoid partial volume effects, a local contrast agent accumulation in vulnerable plaques can be triggered during the acquisition of the data records.

One configuration of at least one embodiment of the invention, in which the additional contrast agent containing iron oxide is embodied such that it adheres to specific ligands of vulnerable plaques, is particularly advantageous. In this case, a particularly reliable identification of vulnerable plaques is possible with the aid of the image data generated.

The possibility of using a single administration of a contrast agent both for the overview and also for the detailed view is particularly advantageous. The effect is used here such that the contrast agent only specifically adheres thereto after some time. To this end, the contrast agent is administered and the overview exposure is produced directly or within a few minutes after the administration, while the contrast agent still circulates in the bloodstream. The detailed exposures are produced afterwards if the contrast agent was adhered to the target region.

In an advantageous configuration of at least one embodiment of the invention, the simulation of the flow conditions includes:

segmentation of the angiography data and identification of vessels and determination of flow speed and vascular wall pressure by way of numerical simulation.

Numerical determination of the said parameters allows the regions with potentially existing pathological changes to be identified and selected for closer examination. This preselection shortens the overall measurement time, since a plurality of regions do not have to be provided here specifically for further examination.

In an advantageous configuration of at least one embodiment of the invention, the determination of the strain on vascular walls has the following method step:

identification of flow type changes and flow speed changes.

Regions with changes in these parameters are potentially endangered. These should thus preferably be selected for additional examinations.

BRIEF DESCRIPTION OF THE DRAWINGS

Further advantages and configurations of the invention result in the example embodiments described below in conjunction with the Figures, in which.

DETAILED DESCRIPTION OF THE EXAMPLE EMBODIMENTS

Figure 1:
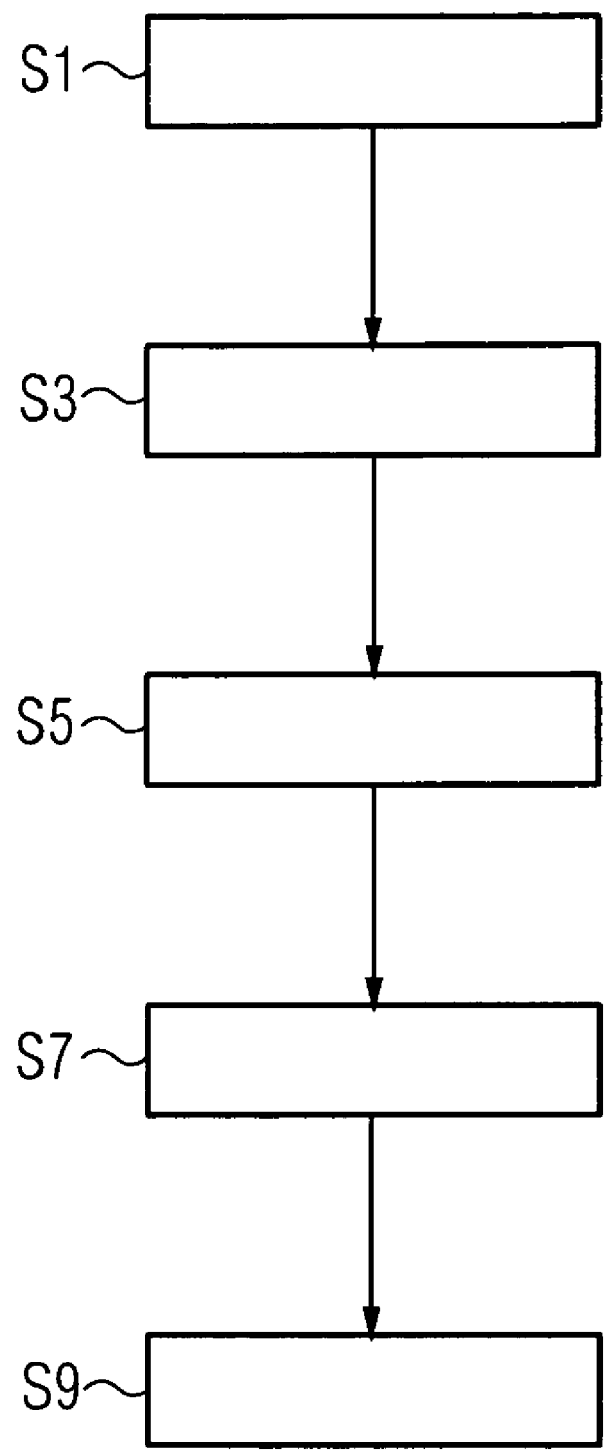
FIG. 1 shows a schematic flow diagram of a method as claimed in one embodiment of the invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a schematic flow chart of an example embodiment of the invention. An overview data record is generated here in a first method step S1. The overview data record was generated by means of an MR angiography and contains angiography data relating to a patient. A VSOP-based contrast agent may have been administered in order to implement the MR angiography for instance. The MR angiography is implemented with a low resolution using the T1 effect of the contrast agent. Alternatively, an angiography can be measured by way of computed tomography. In a second method step S3, the overview data record is segmented and the vascular system of the patient is thus shown isolated. In a third method step S5, the flow conditions within the vascular system are determined by means of numerical simulation calculations. The blood flow speed and the pressure on the vascular walls is calculated in this way. A locally-resolved strain on the vascular walls is determined herefrom. The strain on the vascular walls is compared with a threshold value in a fourth method step S7. The threshold value for the strain on the vascular walls can be predetermined here by a user or may have been determined from preceding measurements. The point at which the strain may result in the formation of vulnerable plaques is taken into consideration here. Risk regions, in which more detailed examinations of the vascular system are needed, can be identified in this way. These detailed examinations therefore take place with a high resolution. Regions in the vascular system in which flow anomalies occur are identified above all as risk regions, said flow anomalies putting significant strain on the vascular walls. Flow anomalies of this type are produced for instance during a transition from a laminar flow in a turbulent flow or during an increase in the flow speed. This can be established from the parameters determined with the aid of the simulations implemented.

In a fifth method step S9, more detailed examinations of the identified risk regions are performed. This is preferably carried out using additional MR examinations, which, contrary to the overview exposures, comprise a smaller field of view and a higher resolution. The use of a contrast agent with VSOP enables vulnerable plaques to be effectively detected within MR examinations. The VSOP are coupled here to specific ligands, which enable an accumulation in vulnerable plaques. Due to the cancellation of the MR signal as a result of the VSOP, the vulnerable plaques are made visible in a simple and efficient manner. The advantage here is in particular that both the angiography for the overview data record and also the detailed examinations of the identified risk regions can be implemented with the same VSOP-based contrast agent. In particular, both methods can be implemented with one single administration of contrast agent. This increases the time efficiency of the overall examinations on the one hand and also reduces the strain on the patient.

During the planning of the digitalized examinations, a dynamic determination is carried out on the basis of the measurement period available as to which risk regions are actually subject to an additional examination. Risk regions with the highest overshooting of the threshold value are first to be measured here. Alternatively, it is possible to dynamically determine the threshold value for the stress of the vascular wall already during the identification of the risk regions thereof and in this way to account for the measurement time which is available for more detailed examinations. The vascular segments are downwardly sorted here according to the risk identified and as many of the risk regions are examined with detailed measurements as is possible during a measurement period which is to be determined beforehand.

Alternatively, the threshold value can be derived from a risk value, which is calculated from laboratory values.

In one alternative embodiment of the invention, the MR angiography is generated by means of time-of-flight or phase contrast measurements.

Figure 2:
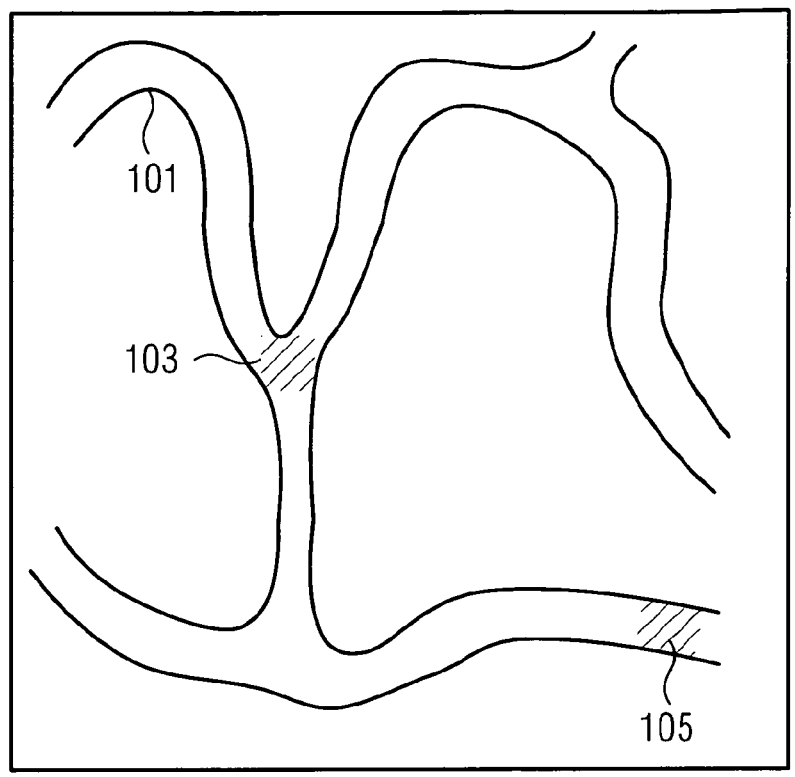
FIG. 2 shows a schematic representation of an angiography and FIGS. 3 and 4 show cutouts of a detailed angiography.
Figure 3:
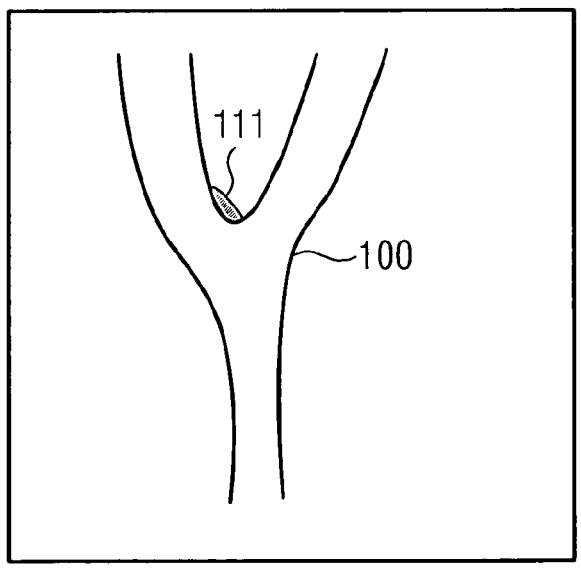
Figure 4:
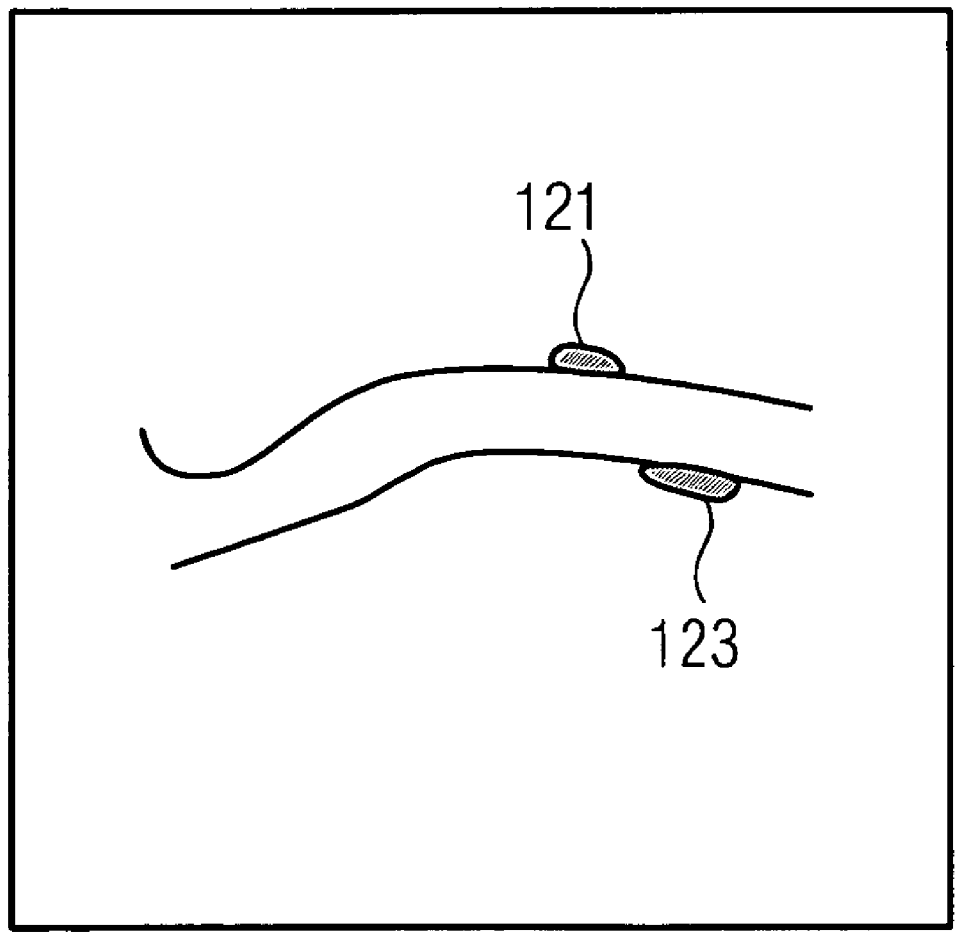

FIG. 2 shows an MR angiography of a vascular system 101. By simulating the flow conditions and determining the strain on the vascular walls by way of the flow, two regions 103 and 105 were identified by way of a threshold value comparison, in which regions the strain on the vascular walls exceeds the threshold value. In two subsequent MR examinations, the identified regions 103 and 105 are examined for the presence of vulnerable plaques. A detailed examination shows the region 103 in FIG. 3. The use of a VSOP-based contrast agent for the detailed examination has visualized a vulnerable plaque 111. FIG. 4 shows a detailed examination of the region 105. Two plaques 121 and 123 could be detected in this region 105. The detailed examinations allow a doctor or radiologist to generate a diagnosis and implement a therapy.

It is also possible to highlight the identified risk areas in color in the representations of the detailed examinations and/or the overview angiography. This allows a doctor or radiologist to gain a good overview in terms of assessing the basic state of health of the patient. It is also possible to determine the cardiac output of the patient from the simulation calculations.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for implementing an imaging examination method comprising:
   creating an overview data record with angiography data relating to a patient;
   simulating flow conditions in vessels of the patient;
   determining a strain on vascular walls with the aid of the simulation;
   identifying vascular regions, in which the determined strain on the vascular wall exceeds a threshold value by comparing the determined strain with the threshold value, an image resolution of the overview data record being lower than an image resolution of the identified vascular regions; and
   implementing an imaging examination in at least one of the identified vascular regions, wherein the overview data record is created by a first MR examination, with a blood circulation of the patient being enforced by a contrast agent containing iron oxide, the identified vascular regions are examined by a second MR examination, with the blood circulation of the patient still being enforced by the contrast agent containing iron oxide and the contrast agent containing iron oxide is embodied such that the contrast agent containing iron oxide adheres to ligands of vulnerable plaque.

2. The method as claimed in claim 1, wherein a plurality of identified vascular regions are examined, with the plurality of the vascular regions being examined in an order of their exceeding of the threshold value.

3. The method as claimed in claim 2, wherein a measurement period is defined for examinations of the identified vascular regions and a number of examinations of vascular regions which is implementable during the measurement period is selected automatically.

4. The method as claimed in claim 2, wherein the identified vascular regions are shown in a graphical overview on a display medium, with a numerical value exceeding of the threshold value of the respective region being highlighted in color.

5. The method as claimed in claim 1, wherein a measurement period is defined for examinations of the identified vascular regions and a number of examinations of vascular regions which is implementable during the measurement period is selected automatically.

6. The method as claimed in claim 1, wherein the identified vascular regions are shown in a graphical overview on a display medium, with a numerical value exceeding of the threshold value of the respective region being highlighted in color.

7. The method as claimed in claim 1, wherein the contrast agent which contains iron oxide contains VSOP.

8. The method as claimed in claim 1, wherein the simulation of the flow conditions includes:
   segmenting the angiography data and identifying vessels; and
   determining flow speed and vascular wall pressure by way of numerical simulation.

9. The method as claimed in claim 1, wherein the determination of the strain on the vascular walls includes:
   identifying flow type changes and flow speed changes.

10. A non-transitory computer readable medium including program segments for, when executed on a computer device, causing the computer device to
   create an overview data record with angiography data relating to a patient,
   simulate flow conditions in vessels of the patient,
   determine a strain on vascular walls with the aid of the simulation,
   identify vascular regions, in which the determined strain on the vascular wall exceeds a threshold value by comparing the determined strain with the threshold value, an image resolution of the overview data record being lower than an image resolution of the identified vascular regions, and
   implement an imaging examination in at least one of the identified vascular regions, wherein the overview data record is created by a first MR examination, with a blood circulation of the patient being enforced by a contrast agent containing iron oxide, the identified vascular regions are examined by a second MR examination, with the blood circulation of the patient still being enforced by the contrast agent containing iron oxide and the contrast agent containing iron oxide is embodied such that the contrast agent containing iron oxide adheres to ligands of vulnerable plaque.

* * * * *